US00PP11821P2

(12) United States Plant Patent
Jonkers

(10) Patent No.: US PP11,821 P2
(45) Date of Patent: Mar. 27, 2001

(54) IMPATIENS PLANT NAMED 'FIFY LAV'

(75) Inventor: J. B. (Hanneke) Jonkers, Hoorn (NL)

(73) Assignee: Goldsmith Plants, Inc., Gilroy, CA (US)

( * ) Notice: Subject to any disclaimer, the term of this patent is extended or adjusted under 35 U.S.C. 154(b) by 0 days.

(21) Appl. No.: 09/078,581

(22) Filed: May 14, 1998

(51) Int. Cl.[7] ..... A01H 5/00

(52) U.S. Cl. ..... Plt./317
(58) Field of Search ..... Plt./317

*Primary Examiner*—Bruce R. Campell
*Assistant Examiner*—Kent L. Bell
(74) *Attorney, Agent, or Firm*—Rothwell, Figg, Ernst & Manbeck

(57) ABSTRACT

A new and distinct cultivar of Impatiens plant, and named 'Fify Lav' is provided. 'Fify Lav' is distinct in its lavender flower color, small slightly cup shaped flowers, early flowering and small-leafed basal branching growth habit.

1 Drawing Sheet

BACKGROUND OF THE NEW PLANT

The present invention comprises a new and distinct cultivar of impatiens, botanically known as *Impatiens walleriana,* and hereinafter referred to by the cultivar name 'Fify Lav', and is characterized by the following combinations of repeatedly observed traits:

1. Very free flowering,
2. Small, single, slightly cup shaped flowers
3. Basal branching with small leaves, and
4. Early flowering.

Asexual reproduction of this cultivar by stem cuttings taken during November, 1996, at Andijk, The Netherlands, has demonstrated that the characteristics of the new cultivar as herein described are firmly fixed and are retained through successive generations of such asexual propagation, such reproduction establishing that the plant does in fact maintain the characteristics described in successive generations. The female parent (i.e., the seed parent) was an *Impatiens walleriana* named IN-1796-3 (unpatented) and the male parent (i.e., pollen parent) was an *Impatiens walleriana* named IN-1444-1 (unpatented). The cross was made in 1995 and the seedling was selected in 1996. The new cultivar is being marketed under the trademark name Fify Lav.

DESCRIPTION OF THE PHOTOGRAPH

This new impatiens plant is illustrated by the accompanying photographic drawings show blooms, buds, and foliage of the plant in full color, the colors shown being as true as can be reasonably obtained by conventional photographic procedures.

DESCRIPTION OF THE NEW CULTIVAR

Figure 1:
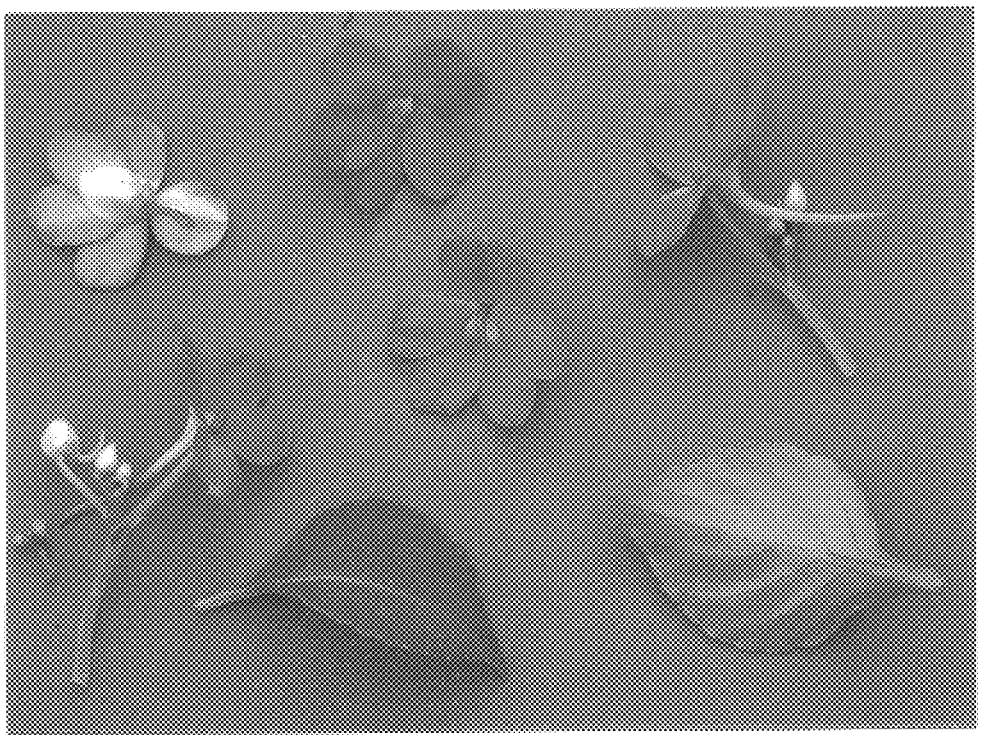
FIG. 1 shows the buds and the upper and lower sides of flower and foliage.
Figure 2:
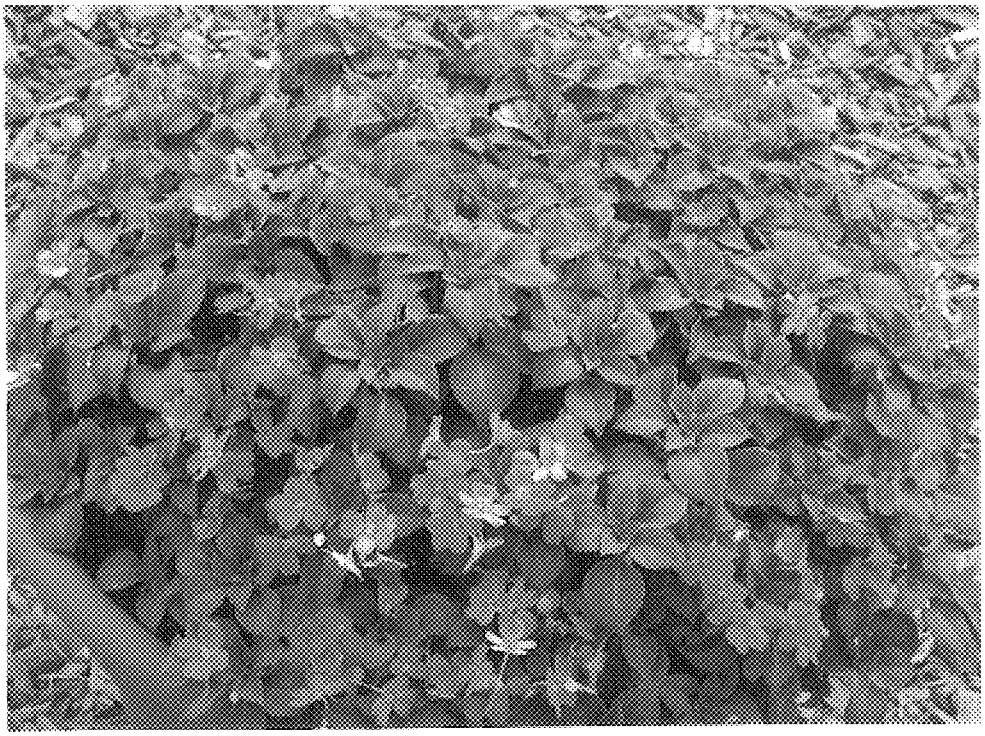
FIG. 2 shows a top perspective view of a typical plant of the new cultivar.

The following observations and measurements describe plants grown outside in the field in Andijk, The Netherlands. Measurements were recorded in August, 1997, on plants approximately 14 weeks old. Fully developed organs were used for measurements and color descriptions, unless otherwise indicated. Color references are made to the R.H.S.

Colour Chart of The Royal Horticultural Society, London, England, except where general color terms of ordinary significance are used.

'Fify Lav' has not been observed under all possible environmental conditions. The phenotype may vary with variations in environment and horticultural practices, such as temperature, light intensity, day length, fertilization and propagation procedure, without any change in genotype.

Parentage:

*Female parent.*—*Impatiens walleriana* IN-1796-3 (unpatented).

*Male parent.*—*Impatiens walleriana* IN-1444-1 (unpatented).

Propagation:

*Type cutting.*—Stem (internodal) cutting with two nodes and attached leaves.

*Time to initiate roots.*—10–14 days at 70–75 degress F. with a fully developed root mass at 21 days.

*Rooting habit.*—Fibrous, branching, adventitious root system.

Plant description:

*Form.*—Upright.

*Growth habit.*—Upright branching plant habit with upper leaves and flowers produced in whorls. When grown in a 4 inch pot for 10–12 weeks the height is approximatley 3–4 inches and the width is approximately 4 inches.

*Foliage description.*—Leaves are simple. Lower leaf arrangement is alternate with upper leaves arranged in whorls of 5. Leaf shape is lanceolate to elliptic with acute apex and obtuse base. Leaf size is 3 cm×1.5 cm. Leaf margin is crenate with ciliation. Leaf surface is glabrous. Leaf color is green. The upper surface is yellow-green group 147A. Under surface is yellow-green group 147B. Venation is pinnate 147A for the upper surface and 147B for the lower surface.

*Petiole.*—Petiole length is 2 cm; and diameter is 0.2 cm; Color is yellow-green 147C.

Flower description:

*Flowering habit.*—Rooted cutting to full flowering plant in six weeks. Indeterminate, flowering continuously. Flowers develop in the upper leaf axils.

*Natural flowering season.*—Flowers continuously throughout the year.

*Flowers borne.*—Singly on pedicels which are yellow-green 145A and 1–1.5 cm long in clusters of 2–7 flowers with a peduncle color of yellow-green 145A and length of 1–1.5 cm long.

*Spur.*—Short spurred; length is 2.5 cm; color of young are 157C to 157D and mature are 158D with apices of 69A.

*Buds.*—Buds are oval-shaped at first color; 145C to 145D and mature buds show 62D before opening; size is 0.8 cm×0.5 cm.

*Quantity of flowers.*—Floriferous. Each axillary cluster of 2–7 flowers developing progressively from the leaf whorls so that buds as well as mature flowers are visible at the same time in large numbers.

*Petals.*—Number of petals 5, with all petals overlapping consisting of 1 round petal approximately 1 cm and 4 oval petals approximately 1.4 cm length and 0.8 cm width. Top three petals are slightly cupped.

*Flower color.*—Upper surface: Purple group 78A fading to 78C with age. Lower surface: Purple group 78D. Occasionally some petals will have white markings or fading of color, 155D, at the basal portion of the petal upper side and on the under side of the petals due to light deficiency from crowded petals.

*Flower size.*—Approximately 2.5 cm wide and 2 cm long.

*Reproductive organs.*—Complete pistil, anthers as cap over the pistil dropping off when flower ages. No pollen.

Disease and Insect Resistance

No known susceptibility to diseases or insects noted to date.

Comparison with the Known Cultivars

When 'Fify Lav' is compared to Impatiens 'Lilac Chico' (unpatented), it is found that 'Fify Lav' exhibits a more vigorous plant habit and is also more floriferous.

When 'Fify Lav' is compared to the IN-1796-3 and IN-1444-1, the parental cultivars, the flower size and plant habit are quite different. 'Fify Lav' has a smaller flower size than either parental cultivars and 'Fify Lav' also has a more compact plant habit than either of the parents.

When 'Fify Lav' is compared to 'Fify Violet', pending U.S. Plant patent application Ser. No. 09/078,656 and 'Fify White', pending U.S. Plant patent application Ser. No. 09/078,641, the main difference is color. The instant cultivar is a lav color while 'Fify Violet' is a reddish-purple and 'Fify White' is a white colored flower.

I claim:

1. A new and distinct cultivar of Impatiens plant named 'Fify Lav', substantially as described and illustrated herein, characterized particularly as to novelty by its lavender flower color, small, slightly cup shaped flowers, early flowering and small-leafed basal branching growth habit.

* * * * *